United States Patent [19]

Munch et al.

[11] Patent Number: 5,284,726
[45] Date of Patent: Feb. 8, 1994

[54] METHOD TO DETERMINE SILVER LOSS IN A PHOTOGRAPHIC EMULSION MANUFACTURING PROCESS

[75] Inventors: William D. Munch, Penfield; Kamala E. Huron, Brockport; Douglas A. Neusch, Rochester, all of N.Y.

[73] Assignee: Eastman Kodak Company, Rochester, N.Y.

[21] Appl. No.: 926,251

[22] Filed: Aug. 6, 1992

[51] Int. Cl.⁵ .................... G03C 5/00; G03C 1/005
[52] U.S. Cl. .................... 430/30; 430/564; 430/569
[58] Field of Search .................... 430/30, 564, 569

[56] References Cited

U.S. PATENT DOCUMENTS

| | | | |
|---|---|---|---|
| 3,752,398 | 8/1973 | Svensson | 239/1 |
| 3,849,197 | 11/1974 | Sorrentino | 134/10 |
| 4,168,700 | 9/1979 | Opelt et al. | 128/630 |
| 4,731,154 | 3/1988 | Hazlitt et al. | 156/626 |
| 4,753,891 | 6/1988 | Thompson et al. | 436/130 |
| 4,919,163 | 4/1990 | Rosenberg | 137/15 |
| 5,022,419 | 6/1991 | Thompson et al. | 134/102 |
| 5,027,841 | 7/1991 | Breunsbach et al. | 134/95 |
| 5,118,596 | 6/1992 | Matushita | 430/430 |

OTHER PUBLICATIONS

"Chemical Separations and Measurements" Peters et al. (1974) pp. 675, 688, 692, 695, 697.

Primary Examiner—John Kight, III
Assistant Examiner—T. Mosley
Attorney, Agent, or Firm—Carl F. Ruoff

[57] ABSTRACT

The present disclosure describes a method called the rinse test for determining where silver is being lost and the variability of this loss in a photographic emulsion manufacturing process. Results from this method can be used to determine what parts of the emulsion manufacturing process should be improved to increase silver yield thereby reducing manufacturing costs and what parts of the emulsion manufacturing process should be improved to reduce silver loss variability thereby improving an emulsion's sensitometric response. The photographic emulsion manufacturing process includes at least one kettle and a plurality of processing equipment which may include sections of pipe, permeators, mixers and pumps. The silver loss is determined by adding water to a kettle after the product has been removed from but prior to cleaning of this kettle. The concentration of silver in this rinse water is measured and the amount of silver is determined. Each piece of processing equipment is flushed sequentially with water from this kettle and the concentration of silver in this rinse water is measured after each piece is flushed. The amount of silver in the receiving kettle is determined then the silver loss in each piece of processing equipment is determined from the incremental increase of the total silver in this rinse water.

10 Claims, 2 Drawing Sheets

સ5,284,726

METHOD TO DETERMINE SILVER LOSS IN A PHOTOGRAPHIC EMULSION MANUFACTURING PROCESS

TECHNICAL FIELD

The present invention is concerned with determining silver loss in a photographic emulsion manufacturing process. More particularly, the present invention is a method for determining which part or parts of an emulsion manufacturing process are the major contributors to the loss of silver and/or high silver loss variability.

BACKGROUND OF THE INVENTION

In the manufacture of photographic emulsions, silver nitrate is typically reacted with halide salts in the presence of gelatin to form a photographically active silver halide. Typical photographic manufacturing processes include the preparation of raw materials in separate kettles (e.g., one kettle for silver nitrate, one kettle for halide salts, one kettle for gelatin, and optional kettles for chemical addenda). After the raw materials are prepared, the silver nitrate and halide salts are transferred at high shear rates into a reaction vessel, usually referred to as the make kettle, which contains water and may contain some gelatin, salts and ripeners. The silver nitrate and halide salts are reacted in the make kettle to form a silver halide suspension, hereafter referred to as an emulsion, containing silver halide grains of a certain size and morphology. This emulsion is typically transferred through a filter after which the emulsion is washed and concentrated. After washing and concentrating the emulsion, the emulsion is transferred into a finish kettle. The concentration of silver in the finish kettle is then determined from which is calculated the total amount of silver in the finish kettle. In many cases, chemical addenda are added to the emulsion in the finish kettle based on the total amount of silver in the finish kettle. These chemical addenda include sensitizing dyes that make an emulsion sensitive to certain wavelengths of light, gelatin to increase the viscosity and achieve certain coating parameters and salts, acids and bases to minimize changes after storage in the final silver halide grain morphology.

In order to manufacture a high quality photographic emulsion as determined by a consistent sensitometric response, the ratio of addenda to silver must be kept as consistent as possible. The more consistent this ratio, the more reproducible will be the amount of addenda adsorbed onto each silver halide grain and the more consistent the sensitometric response of the emulsion. Therefore, sensitometric consistency can be improved by having consistent amounts of silver in the finish kettle.

A second important manufacturing parameter for a photographic emulsion is the quantity of silver as silver halide in the finish kettle. Yields of silver in the finish kettle that approach 100% of the amount of silver prepared in the silver nitrate kettle mean less waste and lower manufacturing costs.

Therefore, both the silver yield and silver yield variability in the finish kettle are important process control parameters that ensure consistent, high quality photographic emulsions manufactured with the lowest possible manufacturing costs. Unfortunately, the silver yield and the silver yield variability in the finish kettle are a result of the silver loss caused by all of the above-described processing steps. If the silver yield in the finish kettle is too low or if the silver loss variability in the finish kettle is too high, it is usually not obvious what part or parts of the emulsion manufacturing process should be improved to reduce the variability and yield problems. It is therefore desirable that the main sources of low silver yield and/or high silver loss variability be identified.

Current methods for determining where silver is lost and where silver loss variability is introduced into an emulsion manufacturing process are to measure the silver yield in each part of the process. For example, once all of the silver nitrate for a batch has been added to the silver nitrate kettle, the concentration of silver times its kettle volume is a measure of the amount of starting silver in the silver nitrate kettle. Once all of the silver is transferred out of the silver nitrate kettle into the make kettle, measurements of the volume and silver concentration of the emulsion in the make kettle can be used to determine how much silver is in the make kettle. The difference between these two measurements is an indication of the silver left in the silver nitrate kettle and the silver nitrate transfer line.

Other measurements that might be used to estimate total silver are the mass of the emulsion based on kettle weigh scales or based on a mass flow meter in a transfer line and a measured density to infer silver concentration. Whatever method is used to determine total silver yield, the problem with these methods is that yields are typically so close to 100% that measuring the silver yields to the needed accuracy of typically less than 0.01% is not practical. These methods of measuring silver yield from each part of the emulsion manufacturing process also cannot be used to differentiate which part of the process is the main cause of the problem.

The present invention is an easily implemented method for determining where silver is being lost in the emulsion manufacturing process and for determining sources of silver loss variability. Once sources of silver loss and/or silver loss variability have been determined, steps can be taken to reduce the problems and thereby increase yields and/or increase the consistency of silver in the finish kettle from one batch to another.

SUMMARY OF THE INVENTION

The present invention, called the rinse test, is a method for determining the location and batch-to-batch variability of silver loss in a photographic emulsion manufacturing process. The photographic manufacturing process includes at least one kettle and a plurality of processing equipment which may include headers, permeators, sections of pipe, mixers and pumps. The method comprises partially filling a kettle with water containing no silver and mixing this water in the kettle after the kettle has been emptied of silver. Note that silver exists as either silver ion in the silver nitrate kettle and silver nitrate delivery lines or as silver halide in all of the other parts of the emulsion manufacturing process. The concentration of silver in the kettle is measured along with the amount of rinse water and the amount of silver is determined.

The rinse water in the kettle is then typically circulated for a predetermined time through one of the plurality of processing equipment and returned to the kettle. Flush water containing no silver is flushed for a predetermined time through one of the plurality of processing equipment from the previous step and added to the water in the kettle. The amount of water in the kettle and the silver concentration are determined and the total amount of silver is calculated. The steps are then repeated for the remaining processing equipment. From this, the amount of silver in each of the plurality of processing equipment is determined. If the rinse test is being run on transfer piping, rinse water from a kettle is typically transferred through the transfer piping into a second kettle where the total amount of silver is determined.

If the rinse test is being run on a ultrafiltration (UF) process, the kettle and all of the piping that feed the permeators are rinsed first. The silver halide is then flushed from the permeators using pulses of silver free water and gas such as compressed air. The flush water is returned to the kettle. The amount of silver in the kettle is then determined based on the amount of rinse water in the kettle and the concentration of silver in the kettle. The incremental amount of silver left in the permeators is then determined.

The determination of the concentration of silver is preferably accomplished by flame atomic absorption spectroscopy.

For a better understanding of the present invention together with other objects, advantages and capabilities thereof, reference is made to the following disclosure and appended claims in connection with the above-described drawing.

DETAILED DESCRIPTION OF THE PREFERRED EMBODIMENTS

Figure 1:
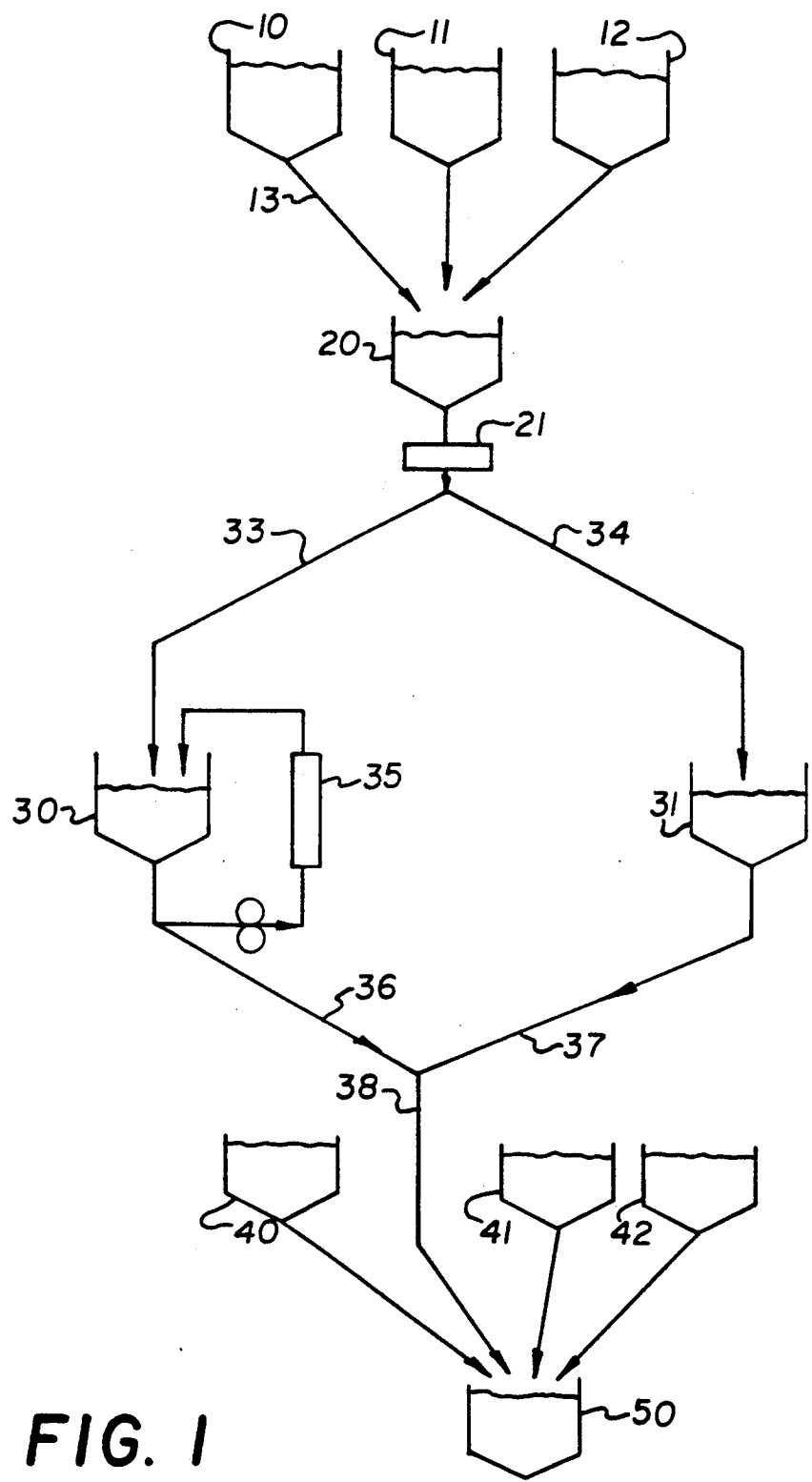
FIG. 1 shows a simplified schematic of an emulsion manufacturing process.

FIG. 1 shows generally an emulsion manufacturing process. The steps included in the manufacturing of photographic emulsion are the preparation of the raw materials in separate kettles 10, 11 and 12. Kettle 10 contains the silver nitrate, kettle 11 contains gelatin and kettle 12 contains one or more halide salts. The raw materials contained in kettles 10, 11 and 12 are transferred at high shear rates into a reaction vessel 20, usually referred to as the make kettle, which contains water and optionally some gelatin, salts or ripeners. As the raw materials are transferred to the make kettle, the silver nitrate reacts with the halide salts to form silver halide grains. The silver halide grains are in a suspension of gelatin and optionally other chemical addenda. Once the silver halide grains are of the proper size and morphology, they are transferred to either of the kettles that do the washing and concentrating. At this point they may be filtered through filter 21 shown on FIG. 1.

The washing and concentrating of the photographic emulsion can be accomplished by an ultrafiltration (UF) membrane process which allows salts, ripeners and other low molecular weight materials to pass through a UF membrane as permeate while retaining large silver halide grains and high molecular weight gelatin in the feed solution. The device that houses the UF membrane is referred to here as a permeator. Optionally, the emulsion may be washed and concentrated using an ISO process which uses changes in pH to precipitate a pH sensitive gelatin allowing ripeners and salts to be decanted off the top of the kettle. Kettle 30 shows the UF process including a UF permeator 35 while kettle 31 shows the ISO process. After washing and concentrating of the photographic emulsion in either the UF kettle 30 or the ISO kettle 31, the emulsion is transferred to a kettle referred to as the finish kettle 50. The concentration of silver is measured in the finish kettle and the total amount of silver is calculated. At this point any chemical addenda including sensitizing dyes, gelatin, salts, acids and bases are added to the emulsion. These additional chemical addenda are stored in kettles 40, 41 and 42.

The present invention called the rinse test is a method of using multiple water rinses through the plurality of processing equipment used to manufacture photographic emulsions as a means of determining where silver is being lost and the batch-to-batch variability of this loss. Each water rinse is run just after a production batch is drained from one of the kettles 10, 20, 30, 31 or 50. The rinse test is run prior to any post water flushes or chemical cleans.

Water is used to rinse out silver either as ionic silver or silver halide from a part of the process. The water is returned to a kettle from which is measured the concentration of silver and the volume or weight of the rinse water collected. The silver concentration times the volume or weight of rinse water is then an estimate of the amount of silver left in various parts of the emulsion manufacturing process. The method typically involves circulating rinse water through a part of the process then using fresh water containing no silver to reclaim all the rinse water containing silver back to the kettle.

This rinse procedure is then followed for all parts of the equipment used to manufacture photographic emulsions (see FIG. 1) and it is repeated for multiple emulsion batches. This test allows one to determine what parts of the emulsion manufacturing process are the major sources of either low silver yield and/or high silver loss variability. These results then suggest what parts of the manufacturing process need to be improved to reduce problems. In addition to showing which parts of the process need to be improved, this test can be used to establish a performance baseline, to determine the degree of improvement of future changes and can be used as an audit tool.

There are a number of events that can occur during the manufacture of photographic emulsions wherein silver is lost such that this loss will not be measured by the rinse test. The rinse test will not measure silver lost to the drain for example through leaky pump seals, leaky valves or due to leaks in the UF membrane. It will not measure any silver that cannot be flushed with water such as silver halide lodged in ball valves or silver halide lodged in dead spots of the UF permeators. Finally, it will not measure the contribution to silver loss and/or silver loss variability due to sampling and testing errors. All of these above-mentioned sources of silver loss and silver loss variability must be measured separately from the present invention.

The simplest application of the rinse test is on the silver nitrate kettle 10, the make kettle 20 and the ISO kettle 31 shown in FIG. 1. In these kettles 10, 20 and 31, silver is processed entirely in the kettle. For these kettles 10, 20 and 31, a predetermined amount of water containing no silver is added to the kettle immediately after the product is transferred out of the kettle. This water is mixed and then sampled. The concentration of silver in this sample is then measured. Finally, the total amount of silver in this rinse water is then calculated from the silver concentration and the amount of water in the kettle.

The second most straightforward application of the rinse test is with all the transfer lines. These transfer lines 13, 33, 34, 36, 37 and 38 include the silver nitrate to make kettle transfer line 13, the make to UF transfer line 33, the make to ISO transfer line 34, the UF to finish kettle transfer line 36 and 38 and the ISO to finish transfer line 37 and 38. For these transfer lines, a predetermined quantity of water containing no silver is passed through the transfer line into a separate empty clean kettle not shown in FIG. 2. Again, this water is mixed then sampled. The concentration of silver in this sample is then measured and the amount of water in the kettle is determined. From these measurements, the total amount of silver collected is then calculated.

Figure 2:
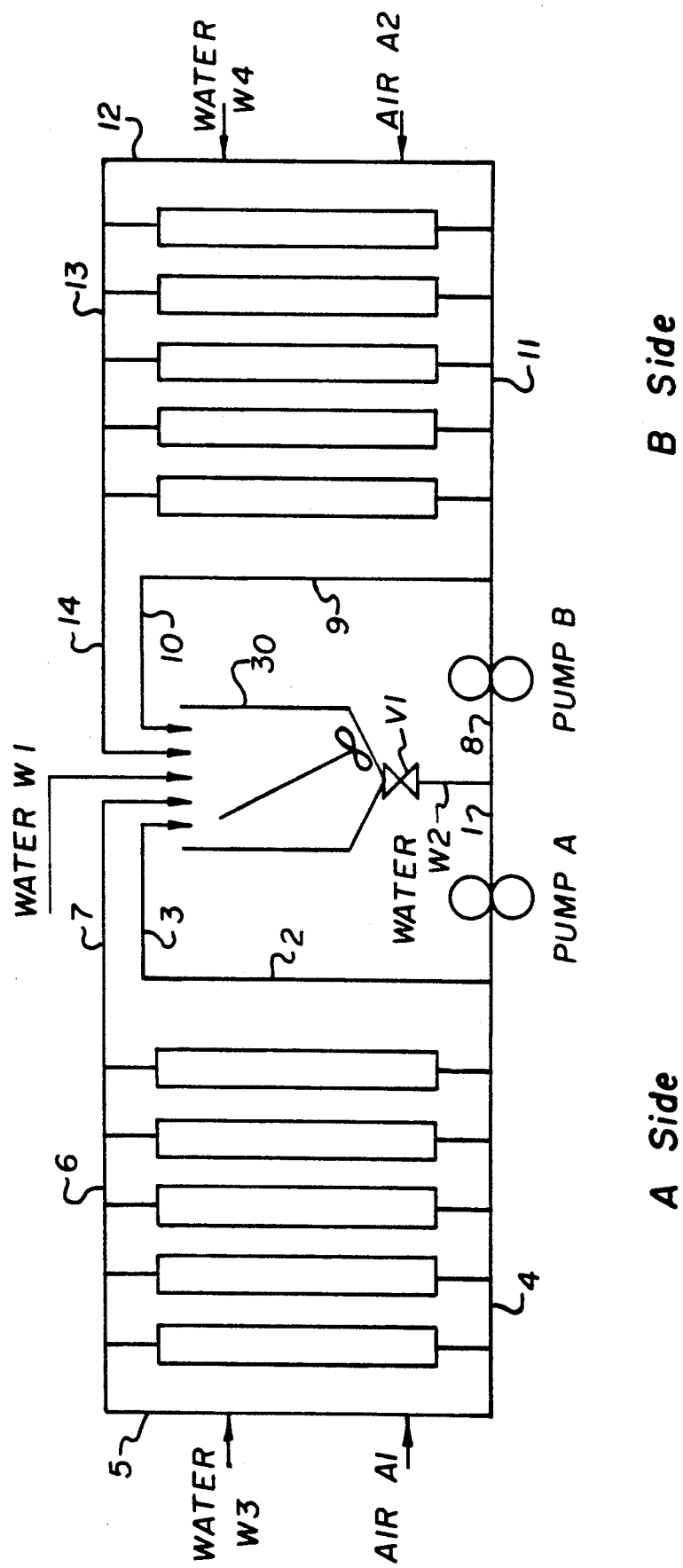
FIG. 2 shows a detailed schematic of an ultrafiltration washing and concentrating process.

The most complex application of the rinse test is in the UF process where emulsion can be left in the UF kettle, the UF piping and/or the UF permeators. The UF process may also have more than one bank of permeators as is shown in FIG. 2 which has an A and a B bank. Note that, although there are many valves used to make the UF process function, none of these valves except the kettle valve V1 are shown in FIG. 2 to simplify the drawing. For the UF process equipment shown in FIG. 2, silver halide may be left in the UF kettle, in piping sections 1–14 and in permeators P1–P10. The preferred embodiment for the rinse test for the UF process is detailed below.

Referring to FIG. 2 the following methodology is used.

1. After the photographic emulsion is transferred out of the UF kettle 30 and before running any water rinses or chemical cleans, a predetermined volume of fresh water is added to the UF kettle using water line W1.
2. A sample of this water is taken from the kettle and the silver concentration of the water is determined. In addition, the volume of water in the kettle is determined.
3. This rinse water in kettle 30 is then circulated through piping sections 1, 2 and 3 for five minutes using pump A.
4. Pipe sections 1, 2 and 3 are flushed with fresh water for 60 seconds by closing the kettle valve V1 and opening water line W2 just beneath the kettle valve, flushing lines 1, 2 and 3 and returning this water to the kettle.
5. The water in the kettle is sampled and analyzed to determine the concentration of silver. In addition, the volume of water in the kettle is determined.
6. The rinse water in the kettle is then circulated through the upper and lower headers, through lines 1, 4, 5, 6 and 7 using pump A.
7. Repeat step 4 to flush lines 1, 2 and 3.
8. Fresh water is flushed through the lower header from water line W3 using lines 5, 4, 2 and 3 and is added to the kettle.
9. Fresh water is flushed through the upper header from water line W3 using lines 5, 6 and 7 and is added to the kettle.
10. The water in the kettle is then analyzed to determine silver concentration and the rinse water volume is recorded.
11. Two gallons of water are then flushed through permeator P1 from water line W3 through lines 5 and 6, permeator P1, lines 4, 2 and 3. This is immediately followed with a 12 second pulse of 40 psi air. This water-air cycle is repeated four times through permeator P1.
12. Step 11 is repeated for permeator P2, then permeators P3, P4 and P5.
13. The rinse water in the kettle is analyzed to determine silver concentration and the volume of rinse water is also determined.
14. Kettle 30 is then drained of the rinse water.
15. Repeat steps 1 and then 3–14 for the corresponding lines and permeators on the B side of the UF unit.

Steps 2, 5, 10 and 13 require the analysis of silver concentration in dilute samples of silver halide which has very little gelatin. Normal analytical methods such as thioacetamide titration cannot be used to measure the silver concentration of these samples since the silver concentration is so low. Also, silver concentrations are difficult to measure for these samples since most of the silver halide quickly settles to the bottom of the sample and is not easily resuspended due to the lack of gelatin. The analytical method used for the rinse test samples which overcomes these difficulties is to convert the silver halide to ionic silver by dissolving the samples in a solution of one molar CNI followed by silver ion measurement by flame atomic absorption spectroscopy. The following procedure is used to measure the silver in the rinse test samples by flame atomic absorption spectroscopy.

1. Allow samples to equilibrate to room temperature.
2. Two types of balances are required to handle the different size samples: a four-place analytical balance (+/− 0.1 mg) and a top loading balance (+/− 0.01 g for weights below 1000 g and +/− 0.1 g for weights of 1000 grams and above) with a maximum weight of 1500 grams.
3. Depending on the size of the sample, weigh each sample and its container on the balance and record its weight. For example, a 60 cc sample and its container can be weighed on a four-place analytical balance while an 8 oz sample and its container can be weighed on a top loading balance.
4. Using an acid-cleaned and dried beaker (e.g., 250 mL beaker for 60 cc sample and 400 mL beaker for 8 oz sample), tare the weight of the beaker on a top loading balance.
5. Pour the sample into the beaker. Using deionized distilled water in a squirt bottle, wash the remaining contents of the container into the beaker. Rinse the container two additional times after all of the contents have been removed into the beaker. In addition, rinse the cap of the container into the beaker.
6. Set aside the cap and the container to air dry. The cap and the container will be weighed at a later time. This weight is then subtracted from the weight obtained in step 3 and provides the weight of the sample.
7. Add one milliliter increments of a 1M CNI solution to the beaker until the mixture becomes clear. Stirring is necessary and can be done with a 3 mL plastic disposable transfer pipet in the inverted position. Be sure to rinse the pipet with deionized distilled water into the beaker.
8. Record the weight of the sample with its washings and CNI. This is the diluted final weight of the sample. Remove the beaker from the balance and cover with a watch glass.
9. Repeat steps 4 through 8 for all of the samples.
10. Using a four-place analytical balance, tare a 50 mL Erlenmeyer flask and a 15 mL disposable plastic centrifuge tube. Aliquots are taken from each beaker. Each aliquot is dispensed into a 15 mL disposable plastic centrifuge tube.

11. Using a 100 microliter pipet, pipet a 100 microliter aliquot into the centrifuge tube. Record the weight (+/− 0.1 mg) of the aliquot. Cap the centrifuge tube with its screw top. Repeat for each aliquot.
12. After all of the aliquots have been weighed into tubes, pipet 9.9 mL using a repipet dispenser of a 0.05M CNI solution into each tube. Shake and invert each tube to insure proper mixing.
13. Prepare three Ag standards at the following concentrations: 5, 10 and 20 micrograms per milliliter (ug/mL) in 0.05M CNI.
14. Allow the air acetylene flame to warm up for 15 minutes. The wavelength for the measurement is 338.3 nm and the concentration mode is used.
15. Calibrate instrument with the standards and run the samples against the standards calibration curve. The samples can be run manually or with an autosampler. If the instrument has the capability to perform calculations to account for dilutions and weights, then use it. It can do most of the calculations but one. The final calculation is dependent on the sample weight and it can be done manually or through a spreadsheet program.
16. Results are reported in milligrams of Ag per gram of sample (mg Ag/g).

In the above procedure, every time a determination is made of the silver concentration, at least three samples are taken and each sample is measured once for silver concentration. This number of samples and number of tests per sample is selected to achieve a certain degree of confidence in the results. Depending upon the desired confidence required, one could take more or fewer samples and run more tests per sample than those specified above.

EXAMPLES

The following gives the results for three rinse tests of the present invention performed on the UF process, each test run after a different batch of emulsion. The emulsion processed was the same emulsion type for each batch. The results are compared to corresponding yield data for the entire emulsion manufacturing process. Each rinse test is run on the A side of the UF unit as shown in FIG. 2. In these examples, no emulsion is found in the UF kettle after the UF process. That is, all silver found via this A side UF rinse test is found in the piping or permeators outside the UF kettle.

After water is circulated through, and then reclaimed from lines 1, 2 and 3, there is 452.5 liters of rinse water in the UF kettle and the silver concentration is measured at 1.169, 1.167 and 1.163 mg Ag/gm solution.

It was assumed that the dilute silver halide solution had a density of about 0.994 kg/L. Thus, the quantity of the silver in the rinse water was 526 grams for sample 1, 525 grams for sample 2 and 523 grams for sample 3. The average amount of silver that was left in lines 1, 2 and 3 was therefore 525 grams. This rinse water was circulated through lines 1, 4, 5, 6 and 7 then reclaimed from these lines with water. Three samples were taken from the UF kettle and the rinse water volume was measured. The total average silver in the kettle was found to be 662 grams of silver. The additional silver due to the A side upper and lower headers was therefore 662 minus 525 or 137 grams of silver.

The silver within the five permeators on the A side of the UF unit was reclaimed using pulses of air and water as described previously. Three samples were taken from the UF kettle and the kettle rinse water volume was measured. The total average silver in the kettle was calculated to be 873 grams. Thus, the additional silver due to the five A side permeators was 211 grams of silver. Therefore, based on this rinse test, a total of 873 grams of silver was collected from the A side of the UF process.

The total amount of silver lost in the entire emulsion manufacturing process is determined by comparing the amount of starting silver in the silver nitrate kettle to the amount of silver in the finish kettle just prior to addenda addition. To make this calculation, one would first measure the concentration of silver and amount of solution in the silver nitrate kettle 10. Using a calculated or estimated density, the total starting amount of silver is determined. In a similar manner, the amount of silver in the finish kettle is determined. Based on the difference between silver in the finish kettle and silver in the silver nitrate kettle, the silver loss is measured as 1600 grams of silver. This suggests that reducing silver losses in the A side of the UF process would reduce overall silver losses for the entire emulsion manufacturing process since silver losses on the A side of the UF process represent approximately 54% of the total silver lost.

Two more rinse tests of the present invention were conducted on the UF process shown in FIG. 2 on the same type of emulsion. The amount of silver for all three rinse tests along with the corresponding total measured silver loss (i.e., based on subtracting silver in the finish kettle from silver in the silver nitrate kettle) is presented in Table 1. Table 1 also includes a calculation of the "sample variance" (i.e., the square of the "sample standard deviation") for these two sets of data. Note that the sample variance of 1,600 gm$^2$ silver from the UF process is much smaller than the sample variance of 12,700 gm$^2$ silver for the entire emulsion manufacturing process. Therefore, for these examples, the A side of the UF process is not a major contributor to the variability of silver in the entire emulsion manufacturing process.

TABLE 1

|  | Test No. 1 (gm) | Test No. 2 (gm) | Test No. 3 (gm) | Sample Variance (gm$^2$) |
|---|---|---|---|---|
| I Silver Lost Per Rinse Test of UF Process | 873 | 823 | 902 | 1600 |
| II Total Silver Lost In Entire Emulsion Manufacturing Process | 1600 | 1485 | 1710 | 12700 |

In summary for this example, the A side of the UF process is a major contributor to emulsion manufacturing silver loss and these losses could best be improved by reducing losses in line 1 of FIG. 2. Also, the A side of the UF process is not a major contributor to the total emulsion manufacture silver loss variability suggesting that other sources of silver loss variability should be investigated if the total manufacturing silver loss variability is to be reduced. This could be accomplished by running rinse tests on other parts of the emulsion manufacturing process.

While there has been shown and described what are at present considered to be the preferred embodiments of the invention, it will be apparent to those skilled in the art that various changes and modifications can be made herein without departing from the scope of the invention as defined by the appended claims.

What is claimed is:

1. A method of determining silver loss in a batch photographic process operation in which a silver photographic emulsion is manufactured, the batch process including at least one kettle and processing equipment comprising sections of pipe, mixers and pumps, the method comprising:
   a) adding water containing no silver to said kettle after said kettle has been emptied;
   b) measuring the amount of water in said kettle and determining the amount of silver in said kettle;
   c) circulating the water in said kettle through one of the processing equipment and returning this circulated water to said kettle;
   d) flushing water containing no silver through one of the processing equipment from step (c) and adding this water to said kettle; and
   e) repeating step (b) through (d) for each of the processing equipment.

2. The method according to claim 1 wherein the amount of silver in each of the processing equipment is determined by an incremental increase in silver in said kettle from step (b).

3. The method according to claim 1 wherein the determination of the amount of silver in step (b) is by flame atomic absorption spectroscopy.

4. The method according to claim 1 wherein the batch photographic process operation is the making of the silver halide emulsion.

5. The method according to claim 1 wherein the batch process further includes one or more permeators, the method of determining silver loss in the one or more permeators comprises:
   f) flushing a predetermined amount of water containing no silver through one of the one or more permeators and then pulsing gas for a predetermined time at a predetermined pressure through one of the one or more permeators and adding this water to said kettle;
   g) repeating step (f) for each of the one or more permeators; and
   h) measuring the amount of water in said kettle and determining the amount of silver in said kettle.

6. The method according to claim 5 wherein the amount of silver in each of the one or more permeators is determined by an incremental increase in silver in said kettle from step (h).

7. The method according to claim 5 wherein the determination of the amount of silver in step (h) is by flame atomic absorption spectroscopy.

8. A method of determining silver loss in a batch photographic process operation in which a silver photographic emulsion is manufactured, the batch process including at least one kettle and processing equipment comprising sections of pipe, UF permeators, mixers and pumps, the method comprising:
   a) adding water containing no silver to said kettle after said kettle has been emptied;
   b) measuring the amount of water in said kettle and determining the amount of silver in said kettle;
   c) circulating the water in said kettle through one of the processing equipment except for the UF permeators and returning this circulated water to said kettle;
   d) flushing water containing no silver through one of the processing equipment from step (c) and adding this water to said kettle;
   e) repeating steps (b) through (d) for each of the processing equipment except for the UF permeators;
   f) flushing a predetermined amount of water containing no silver through one of the permeators and then pulsing gas for a predetermined time at a predetermined pressure through the permeator;
   g) repeating step (f) for each permeator;
   h) measuring the amount of water in said kettle and determining the amount of silver in said kettle;
   i) determining the amount of silver in each of the processing equipment by determining the incremental amount of silver after each of the silver measurements in step (b) and step (h).

9. The method according to claim 8 wherein the batch photographic process operation is the filtration of the silver halide emulsion.

10. The method according to claim 8 wherein the determination of the amount of silver in step (b) and (h) is by flame atomic absorption spectroscopy.

* * * * *